(12) United States Patent
Miyajima et al.

(10) Patent No.: US 7,731,714 B2
(45) Date of Patent: Jun. 8, 2010

(54) INSTRUMENT FOR ENDOSCOPE AND INSTRUMENT SYSTEM FOR ENDOSCOPE

(75) Inventors: Chika Miyajima, Tokyo (JP); Tsutomu Nakamura, Tokyo (JP)

(73) Assignee: Olympus Corporation (JP)

( * ) Notice: Subject to any disclaimer, the term of this patent is extended or adjusted under 35 U.S.C. 154(b) by 1048 days.

(21) Appl. No.: 11/441,731

(22) Filed: May 26, 2006

(65) Prior Publication Data
US 2006/0276784 A1    Dec. 7, 2006

(30) Foreign Application Priority Data
May 30, 2005    (JP)    .......................... P2005-157050

(51) Int. Cl.
*A61B 18/14*    (2006.01)
(52) U.S. Cl. .............................. 606/46; 606/45; 606/49
(58) Field of Classification Search ................... 606/45, 606/49, 46
See application file for complete search history.

(56) References Cited

U.S. PATENT DOCUMENTS

| | | | |
|---|---|---|---|
| 4,682,596 A | | 7/1987 | Bales et al. |
| 4,708,137 A | | 11/1987 | Tsukagoshi |
| 5,158,561 A | * | 10/1992 | Rydell et al. .................. 606/49 |
| 5,441,499 A | * | 8/1995 | Fritzsch ....................... 606/45 |
| 6,056,744 A | | 5/2000 | Edwards |
| 7,517,347 B2 | * | 4/2009 | Hug et al. ..................... 606/45 |
| 2004/0210215 A1 | | 10/2004 | Okada |
| 2004/0210284 A1 | | 10/2004 | Okada |

FOREIGN PATENT DOCUMENTS

| | | |
|---|---|---|
| JP | S55-125858 | 9/1980 |
| JP | H5-337130 | 12/1993 |
| WO | WO2004/110294 | * 12/2004 |

OTHER PUBLICATIONS

Search Report issued by the European Patent Office dated Apr. 26, 2007.
Letter from Foreign Associates reporting the European Search Report dated May 22, 2007.

* cited by examiner

*Primary Examiner*—Lee S Cohen
(74) *Attorney, Agent, or Firm*—Ostrolenk Faber LLP (57) ABSTRACT

An instrument for an endoscope including a flexible insulative insertion section inserted in an endoscope channel, a tubular first electrode section arranged at a distal end of the insertion section with an insertion hole formed along the axis of the insertion section, a conductive electric wire inserted in the insertion section and movable forward/backward, a control section arranged on the proximal end side of the insertion section and controlling forward/backward movement of the electric wire along the axis, a rod-shaped second electrode section connected to a distal end of the electric wire and inserted so as to be movable forward/backward in the insertion hole, and an external connecting section electrically connected to a proximal end side of the electric wire and applying external currents with predetermined frequencies to the electric wire and the second electrode section.

6 Claims, 9 Drawing Sheets

INSTRUMENT FOR ENDOSCOPE AND INSTRUMENT SYSTEM FOR ENDOSCOPE

CROSS-REFERENCE TO RELATED APPLICATION

This application claims the benefit of the filing date of Japanese Patent Application No. 2005-157050 filed 30 May 2005, the disclosure of which is hereby incorporated by reference

BACKGROUND OF THE INVENTION

1. Field of the Invention

The present invention relates to an instrument for an endoscope such as a high frequency knife for resecting living tissues, in particular, a high frequency knife used for endoscopic submucosal dissection (hereinafter abbreviated as "ESD"), and also to an instrument system for an endoscope having the instrument for an endoscope.

2. Description of Related Art

Treatments for resecting living tissues such as mucosa using endoscopes have been performed conventionally and ESD such as resecting lesions formed on the surface of the digestive tract by dissecting submucosa to resect the affected area after circumferential incision of normal mucosa in the outer side of the affected area has been carried out.

When carrying out ESD, bleeding often occurs when circumferentially incising mucosa or exfoliating submucosal layer. Therefore, there is a need to perform procedures while carrying out dissection treatment and bleeding coagulation treatment alternately at appropriate timing.

When dissection of living tissue is carried out, the living tissue is locally cauterized and dissected by applying high frequency current (current for dissection) to an electrode section such as a scalpel whose contact area with the living tissue is small. On the other hand, when performing coagulation treatment for bleeding, the bleeding site and the living tissue around it is cauterized to carry out blood coagulation procedures by applying a current different from the one applied at the time of dissection (current for coagulation) to an electrode section with a shape such as of a sphere whose contact area with the living tissue is large.

As described so far, it is necessary to apply currents with different frequencies (waveforms) to electrode sections with different shapes in order to carry out dissection and coagulation treatments.

Although it is possible to apply currents for dissection and coagulation respectively to one electrode section, when applying the current for coagulation to an electrode section such as a scalpel with a small contact area with the living tissue, there is a concern that resection may be carried out without coagulation because of high energy density. On the other hand, when applying the current for dissection to an electrode section with a large contact area with the living tissue, resection may be impossible due to low energy density.

Accordingly, as described above, it is necessary to use two electrode sections which are different from each other for carrying out dissection and coagulation treatments, respectively.

Thus, conventionally, in order to perform dissection and coagulation treatments during ESD, there has been no alternative but to use an instrument for dissection and an instrument for coagulation having respective electrode sections at distal ends thereof alternately by interchanging them in the channel of endoscope.

Accordingly, it inevitably takes time to exchange the instruments and the procedures take more time, resulting in heavy burden on the patients. Moreover, it has been difficult to perform rapid hemostasis treatment at the bleeding site because of the time spent until the coagulation treatment is carried out.

Thus, an electrode rod for resection (refer to patent document 1, for instance) capable of shortening the time spent on dissection and coagulation treatments, a single pole polyp resecting snare provided with a coagulation electrode (refer to patent document 2, for instance), and the like are known for resolving such inconveniences.

The electrode rod for resection described in patent document 1 is equipped with electrodes for both dissection and coagulation at the distal end of the main body thereof. Therefore, it is possible to apply current to both electrodes simultaneously by applying current to a conducting section provided on the proximal end side of the electrode rod main body. It is possible to carry out dissection and coagulation treatments rapidly by making the respective electrodes contact the living tissue alternately.

In addition, the single pole polyp resecting snare provided with a coagulation electrode described in patent document 2 is equipped with a ring-shaped surface electrode (electrode for coagulation) with a large contact area with the living tissue at the distal end of a tubular plastic member. Moreover, it is provided with a conductive snare loop (electrode for dissection) arranged so as to be freely movable forward and backward inside the plastic member and capable of ligating living tissues. Furthermore, the surface electrode and loop are electrically connected to cords having plugs at their ends so as to be connectable separately to jacks of their electrosurgical oscillator.

According to this single pole polyp dissecting snare provided with a coagulation electrode, rapid dissection and coagulation treatments can be carried out by merely exchanging plugs connected to respective cords of the surface electrode and loop to the jacks of an electrosurgical oscillator.

[Patent Document 1] Japanese Unexamined Patent Application, First Publicaion No. Sho 55-125858

[Patent Document 2] Japanese Unexamined Patent Application, First Publicaion No. Hei 5-337130

However, the problems below remained unresolved with the inventions described in the above patent documents 1 and 2.

When the current is applied to the conductive section in the electrode rod for resection described in patent document 1, the current is applied to the electrode sections for both dissection and coagulation. Accordingly, for instance, there is the possibility of damaging untargeted parts when the electrode section for dissection unexpectedly contacts living tissue while carrying out blood coagulation at the bleeding site. Therefore, it is hard to use and puts excessive strain on the operator. In addition, it is impossible to apply current with different frequencies to the electrode sections for dissection and coagulation, and there is the concern of inappropriate dissection or blood coagulation treatment.

On the other hand, although it is possible to solve the aforementioned disadvantages by using the single pole polyp resecting snare provided with a coagulation electrode described in patent document 2, there is a need to exchange plugs plugged into the electrosurgical oscillator every time the surface electrode or loop is used. Accordingly, although not as much as when exchanging instruments, it is still laborious to exchange jacks resulting in the inconvenience of longer hours spent for ESD. Thus, there is a heavy burden on the patient.

The present invention was made by taking the aforementioned problems of the prior art into consideration and its object is to provide an instrument for an endoscope and an instrument system for an endoscope which make it possible to perform dissection and coagulation treatments by rapidly using electrode sections with appropriate shapes for each purpose separately, which require less labor, and also capable of reducing the burden on the patient by shortening the time spent for the procedures.

SUMMARY OF THE INVENTION

The present invention provides the means below in order to achieve the above objects.

The invention according to a first aspect provides an instrument for an endoscope having an insulative insertion section inserted in a channel of an endoscope and having flexibility, a tubular first electrode section arranged at the distal end of the insertion section and on which an insertion hole is formed along the axis of the insertion section, a conductive electric wire inserted in the insertion section so as to be freely movable forwards and backwards, a control section arranged on the proximal end side of the insertion section and controlling forward/backward movement of the electric wire along the axial direction, a rod-shaped second electrode section connected to the distal end of the electric wire and inserted so as to be freely movable forwards and backwards inside the insertion hole, and an external connecting section electrically connected to the proximal end side of the electric wire and applying external currents with predetermined frequencies to the electric wire and the second electrode section, wherein the second electrode section protrudes from and retracts into the distal end of the first electrode section in response to the movement control by the control section, and also electrically connects with the first electrode section when retracted into the first electrode section.

The invention according to a second aspect provides the instrument for an endoscope according to the first aspect, wherein the first electrode section is formed so that an inner circumferential surface thereof is in an electrically insulative state.

The invention according to a third aspect provides the instrument for an endoscope according to the first or second aspect, having a recess formed at the distal end of the first electrode section so as to surround the periphery of the opening of the insertion hole, and a salient arranged at the distal end of the second electrode section and which extends in the direction perpendicular to the axial direction, wherein the salient is contained in the recess when the second electrode section retracts into the first electrode section.

The invention according to a fourth aspect provides the instrument for an endoscope according to the third aspect, having a stopper member which is arranged in-between the electric wire and the second electrode section, which contacts the proximal end side of the first electrode section to regulate the extent of protrusion of the second electrode section when the second electrode section protrudes and which provides insulation to the first electrode section when it makes contact with the proximal end side of the first electrode section.

The invention according to a fifth aspect provides the instrument for an endoscope according to any of the first to third aspects, having a conductive stopper member arranged in-between the electric wire and the second electrode section and contacting the proximal end side of the first electrode section when the second electrode section protrudes to regulate the extent of the protrusion of the second electrode section, and an electrically connecting section electrically connecting the stopper member and the first electrode section when the second electrode section is retracted, wherein a contact surface of the first electrode section which contacts the stopper member when the second electrode section protrudes is formed in an electrically insulated state.

The invention according to a sixth aspect provides the instrument for an endoscope according to the fifth aspect, wherein the second electrode section is a needle-shaped member.

The invention according to a seventh aspect provides the instrument for an endoscope according to any one of the first to sixth aspects, wherein the first electrode section has a distal end surface parallel to the surface perpendicular to the axial direction.

The invention according to an eighth aspect provides the instrument for an endoscope according to any one of the first to seventh aspects, wherein the first electrode section is formed so that the entire outer circumferential surface is in an electrically insulative state.

The invention according to a ninth aspect provides an instrument system for an endoscope having an instrument for an endoscope according to any of the first to eighth aspects, detection means for determining the position of the control section in the moving direction, a current applying section electrically connected to the external connecting section and applying the currents with predetermined frequencies, a switch for operating the current applying section at an arbitrary timing, and a regulating section automatically changing the current output settings of the current applying section based on the determination made by the detection means.

DETAILED DESCRIPTION OF THE INVENTION

The first embodiment of the instrument for an endoscope according to the present invention will be described below with reference to FIGS. 1 to 5.

Figure 1:
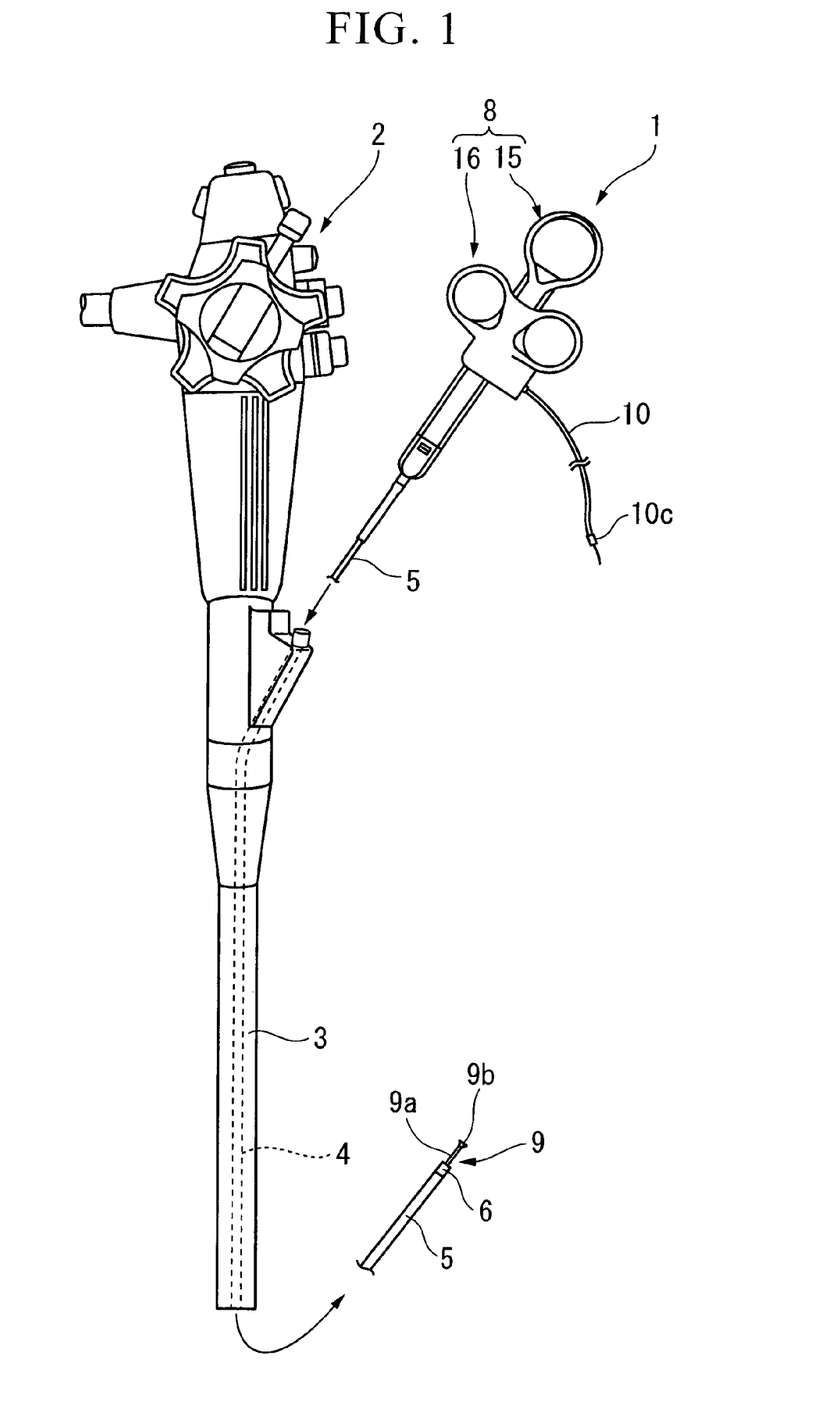
FIG. 1 is a diagram showing a first embodiment of the high-frequency knife according to the present invention, where the knife is inserted in an endoscope instrument channel.
Figure 2:
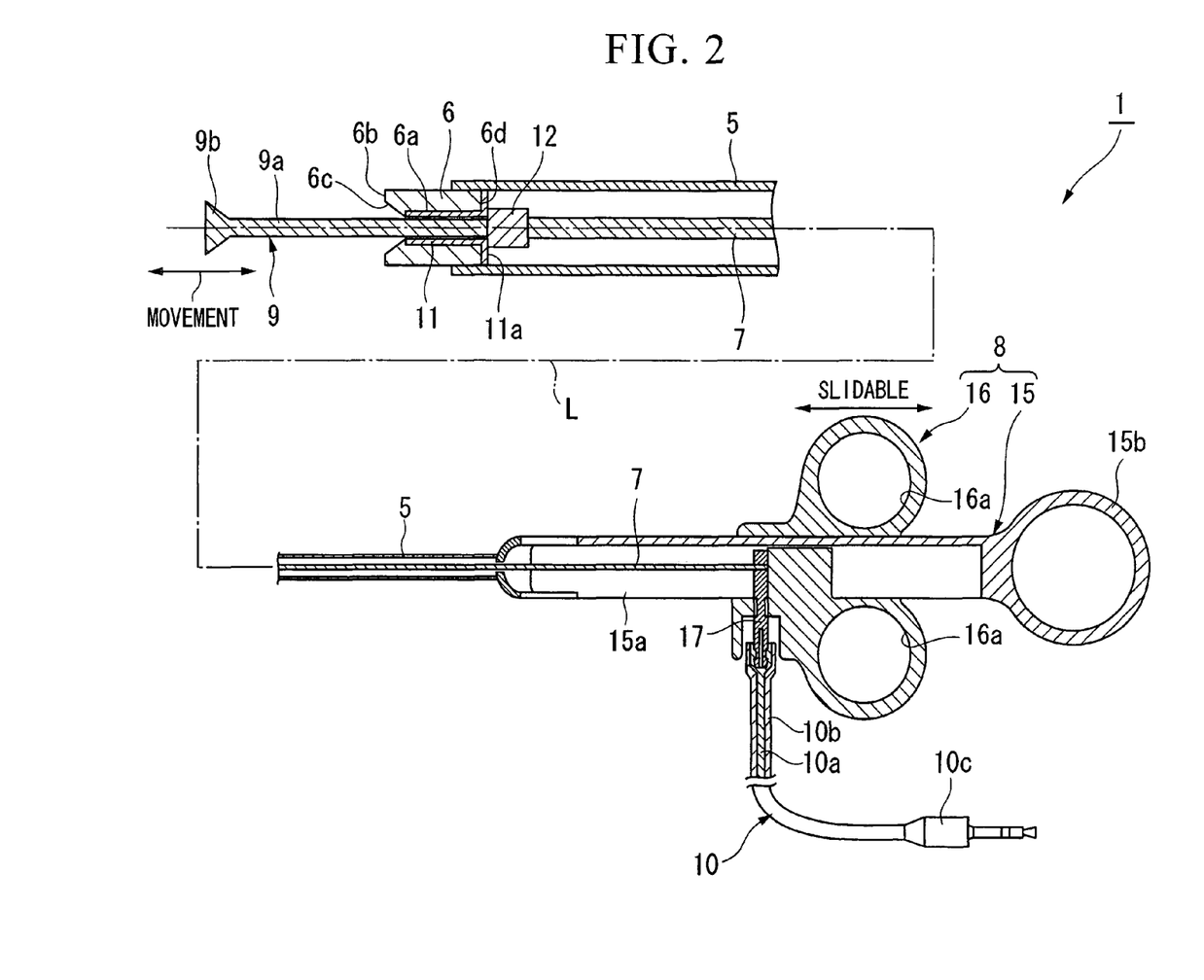
FIG. 2 is a cross section of the high-frequency knife shown in FIG. 1, where a second electrode section is protruding from a distal end of a first electrode section.
Figure 3:
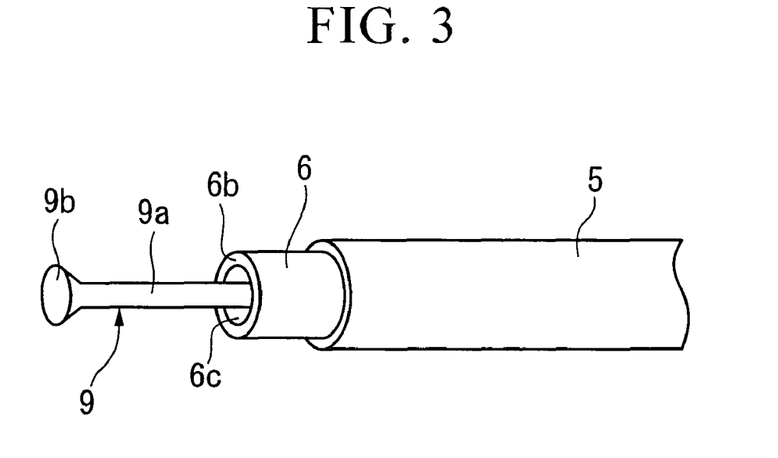
FIG. 3 is an enlarged perspective view of a distal end side of the high-frequency knife shown in FIG. 2.

As shown in FIGS. 1 to 3, the high-frequency knife (instrument for an endoscope) 1 of the present embodiment has an insulative insertion section 5 inserted in an instrument channel (channel) 4 formed in an endoscope insertion section 3 of an endoscope 2 and having flexibility, a tubular first electrode section 6 arranged at the distal end of the insertion section 5 and in which an insertion hole 6a is formed along an L axis of the insertion section 5, a conductive control wire (electric wire) 7 inserted so as to be freely movable forward and backward in the insertion section 5, a control section 8 arranged in the proximal end side of the insertion section 5 and controlling the movement of the control wire 7 along the L axis direction, a rod-shaped second electrode section 9 connected to the distal end of the control wire 7 and inserted so as to be freely movable forward and backward in the insertion hole 6a, and a connecting cord (external connecting section) 10 electrically connected to the proximal end side of the control wire 7, which applies an external current (current for dissection or coagulation) with a predetermined frequency to the control wire 7 and the second electrode section 9.

The insertion section 5 is a long tubular body and the proximal end side thereof is fixed to the distal end side of a control section main body 15 of the control section 8, described later. Moreover, the first electrode section 6 is fixed on the inner circumferential surface in the distal end side of the insertion section 5 so as to protrude from the distal end of the insertion section 5. This first electrode section 6 has a distal end surface 6b parallel to a surface perpendicular to the L axis direction of the insertion section 5 and formed into a pipe-shape with a circular section extending towards the L axis direction. A taper shaped recess 6c is formed so as to surround the periphery of the opening of the insertion hole 6a in the distal end surface 6b. Moreover, an insulating member 11 is provided in the inner circumferential surface (excluding an inner circumferential surface of the recess 6c) of the first electrode section 6 and the proximal end surface (contact surface) 6d in a state where it is electrically insulated.

The control wire 7 is inserted throughout the insertion section 5 from the distal end side to the proximal end side and a conductive stopper member 12 is connected at the distal end side thereof. This stopper member 12 is formed into a column shape with an outer diameter larger than that of the control wire 7 and, when the control wire 7 moves to the distal end side, moves together with the control wire 7 so as to contact a proximal end surface 11a of the insulating member 11 positioned in the proximal end surface 6d side of the first electrode section 6.

Figure 4:
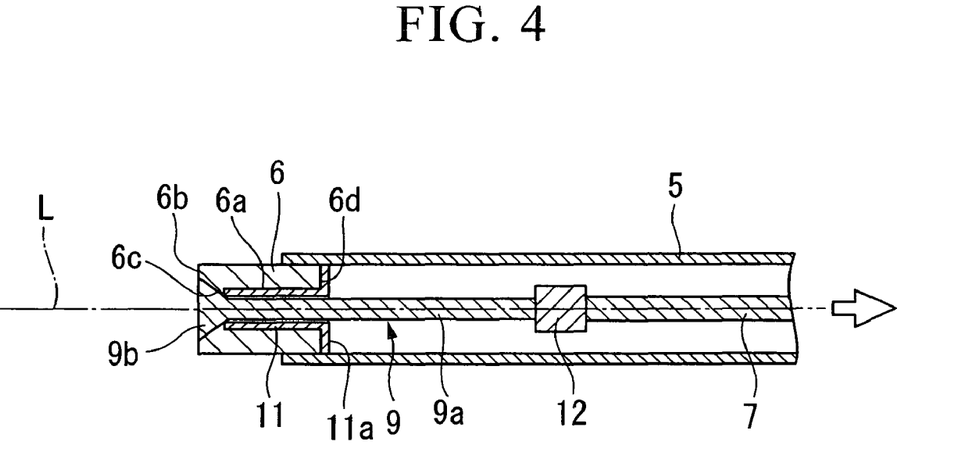
FIG. 4 is an enlarged cross section of the distal end side of the high-frequency knife shown in FIG. 1, where the second electrode section is retracted into the first electrode section.

A rod-shaped section 9a which has a circular section extending towards the L axis direction and whose proximal end side is connected to the stopper member 12, integrally forms the second electrode section 9 with a salient 9b, which is arranged at the distal end of the rod-shaped section 9a and extends in the direction perpendicular to the L axis direction. Moreover, this salient 9b is formed into a shape so as to be contained in the recess 6c when the second electrode section 9 retracts into the first electrode section 6 as shown in FIG. 4 and at the same time, made so as not to protrude from the distal end surface 6b when contained so that the smoothness of the distal end surface 6b is ensured.

That is, the second electrode section 9 protrudes from and/or retracts into the distal end of the first electrode section 6 in response to the movement control of the control wire 7 by the control section 8 and is also made so as to be electrically connected to the first electrode section 6 when retracted into the first electrode section 6. In other words, the second electrode section 9 retracts into the first electrode section 6 and at the same time the salient 9b is contained in the recess 6c as described above when the control wire 7 moves to the proximal end side of the insertion section 5. The outer circumferential surface of the salient 9b and the inner circumferential surface of the recess 6c contact due to this process so as to electrically connect the first electrode section 6 and the second electrode section 9.

Moreover, as shown in FIG. 2, the stopper member 12 contacts the proximal end surface 11a of the insulating member 11 when the control wire 7 moves to the distal end side of the insertion section 5, thereby working to regulate the extent of protrusion of the second electrode section 9.

As shown in FIG. 2, the control section 8 has an almost axis shaped control section main body 15 and a sliding section 16 which is capable of movement control (sliding) in the L axis direction relative to the control section main body 15. Moreover, the control section main body 15 and sliding section 16 are formed from non-conductive materials such as plastic. In addition, a guide groove 15 a of the sliding section 16 is formed in the control section main body 15 in the L axis direction and the sliding section 16 is installed so as to slide along the guide groove 15 a. Furthermore, the proximal end side of the control wire 7 is connected to the sliding section 16. Thereby, the movement of the control wire 7 is controlled when the sliding of the sliding section 16 is controlled along the guide groove 15a so that the second electrode section 9 protrudes from and/or retracts into the distal end of the first electrode section 6 as described above.

Moreover, a finger hooking ring 15b where the thumb can be inserted is attached at the proximal end side of the control section main body 15 and similarly, finger hooking holes 16a where the index and middle fingers can be inserted are formed in the sliding section 16. The operator can readily control the control section 8 by one hand using them.

Furthermore, a connection terminal 17 electrically connected to the proximal end of the control wire 7 is arranged in the sliding section 16 and one end side of a wire 10a of the connecting cord 10 is connected to the connection terminal 17. Note that the wire 10a is covered by the insulative tube 10b. Additionally, a plug 10c pluggable into a connecting jack 21 of a high-frequency power source 20 is provided in the other end side of this connecting cord 10.

Figure 5:
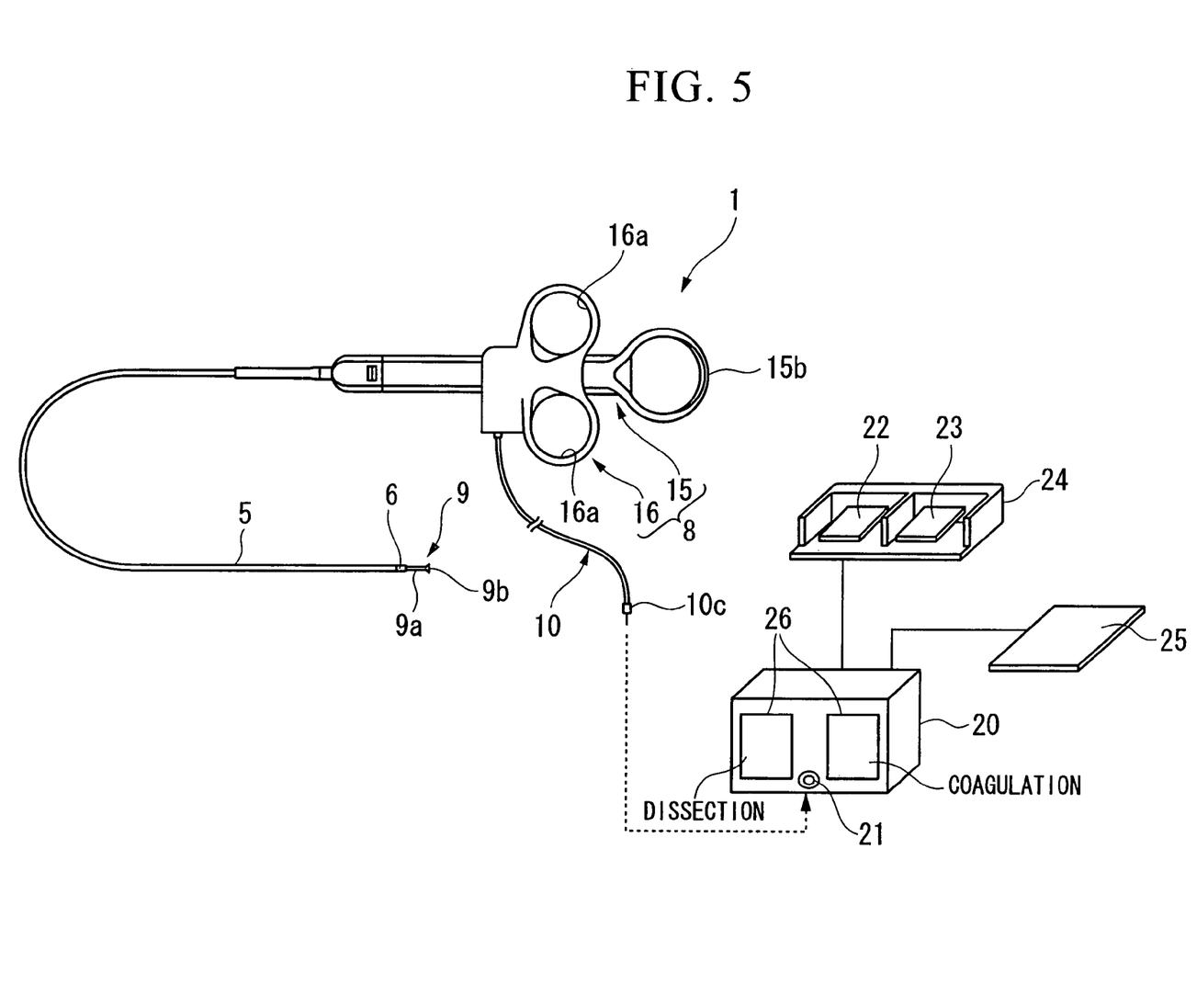
FIG. 5 is a diagram showing the state where the high-frequency knife shown in FIG. 1 is connected to a high frequency power source.

A foot switch 24 where a pedal switch for dissection 22 and a pedal switch for coagulation 23 are provided and a return electrode 25 laid under the patient during the procedure are connected to the high-frequency power source 20 as shown in FIG. 5. Moreover, a current applying section 26 applying the current for dissection to the connecting cord 10 only when the operator sets a foot on the pedal switch for dissection 22 and applying the current for coagulation to the connecting cord 10 only when the operator steps on the pedal switch for coagulation 23, is internally installed in the high-frequency power source 20.

A case where living tissue is excised by the high-frequency knife 1 configured as such will be described next. It should be noted that ESD performed when an affected area not shown formed in the surface of the digestive tract is excised by removing the submucosal layer will be taken as an example for the description in the present embodiment.

Firstly, after the return electrode 25 is set under the patient, an endoscope insertion section 3 is inserted in the celom to position the distal end thereof in the vicinity of the affected area. Then an injection needle, not shown, is introduced in the celom via an instrument channel 4 and the affected area is expanded by locally injecting physiological saline into the submucosal layer in the vicinity of the affected area. Subsequently, a hole is made in the part of mucosa in the vicinity of the affected area, from which circumferential incision will start, using a conventional needle-shaped high-frequency knife 1, not shown.

Then the insertion section 5 of the high-frequency knife 1 of the present embodiment is inserted in the instrument channel 4 so that it protrudes from the distal end of the endoscope insertion section 3 as shown in FIG. 1. At this time, the insertion section 5 is inserted in a state where the sliding section 16 is moved to the proximal end side relative to the control section main body 15 and the second electrode section 9 is retracted into the first electrode section 6 as shown in FIG. 4.

After the insertion section 5 protrudes from the distal end of the endoscope insertion section 3, the sliding section 16 is moved to the distal end side relative to the control section main body 15 and the second electrode section 9 protrudes from the distal end of the first electrode section 6 as shown in FIGS. 2 and 3. At this time, the sliding section 16 is moved to the distal end side until it will not move any more, in other words, until the stopper member 12 contacts the proximal end surface 11a of the insulating member 11. Since the extent of protrusion of the second electrode section 9 is regulated by this process, the second electrode section 9 reliably protrudes by a predetermined length. Therefore, since the second electrode section 9 will not unexpectedly protrude more than necessary at the time of performance of the following dissection treatment, safety can be enhanced at the time of the dissection treatment.

After the second electrode section 9 protrudes, the entire insertion section 5 or the entire endoscope insertion section 3 is moved to insert the salient 9b and rod-shaped section 9a of the second electrode section 9 in the hole made in the mucosa in the vicinity of the affected area. After confirming this state, the operator steps on the pedal switch for dissection 22. When the pedal switch for dissection 22 is stepped on, the current applying section 26 applies the current for dissection to the connecting cord 10 as long as the pedal switch is held down. The current for dissection is applied to the second electrode section 9 via the connecting cord 10, control wire 7, and stopper member 12. Thus, the living tissue contacting the salient 9b and rod-shaped section 9a can be locally cauterized and dissected.

In particular, since the second electrode section 9 is rod-shaped, with a relatively small contact area with the living tissue, the dissection treatment can be performed reliably using the current for dissection while enhancing energy density.

Moreover, at the time of the dissection treatment described above, since the proximal end surface 6d of the first electrode section 6 is in an insulated state due to the presence of the insulating member 11, the current for dissection is not applied via the stopper member 12. Furthermore, since the inner circumferential surface of the first electrode section 6 is similarly in an insulated state due to the presence of the insulating member 11, the current for dissection is not applied to the first electrode section 6 at the time of carrying out of the dissection treatment even if the insertion hole 6a and the second electrode section 9 contact.

Therefore, the dissection treatment can be carried out safely without any problems even when the second electrode section 9 contacts the instrument channel 4 or living tissue during the dissection treatment.

The mucosa surrounding the affected area, with the affected area in the center, is circumferentially incised in the dissection treatment using the second electrode section 9. Especially, since the salient 9b is arranged on the distal end of the second electrode section 9, it is possible to dissect while hooking the mucosa onto the salient 9b, and thus, the dissection treatment is easily performed.

When the bleeding is observed while performing the aforementioned dissection treatment at this stage, the operator moves the sliding section 16 to the proximal end side of the control section main body 15 to retract the second electrode section 9 into the first electrode section 6 after removing his foot from the pedal switch for dissection 22 to stop the application of the current for dissection as shown in FIG. 4. The salient 9b of the second electrode section 9 is completely contained in the recess 6c of the first electrode section 6 due to this retracting and the smoothness of the distal end surface 6b is reliably ensured. Moreover, since the outer circumferential surface of the salient 9b contacts the inner circumferential surface of the recess 6c, the first electrode section 6 and the second electrode section 9 are electrically connected.

After retracting the second electrode section 9, the operator moves the entire insertion section 5 or the entire endoscope insertion section 3 and presses the distal end surface 6b of the first electrode section 6 (including the distal end of the salient 9b of the second electrode section 9) against the living tissue including the bleeding site. After confirming this state, the operator steps on the pedal switch for coagulation 23. When the pedal switch for coagulation 23 is stepped on, the current applying section 26 applies the current for coagulation to the connecting cord 10 as long as the pedal switch for coagulation 23 is held down. This current for coagulation is applied to the first electrode section 6 via the connecting cord 10, control wire 7, stopper member 12 and second electrode section 9. As a result, it is possible to carry out coagulation treatment to stop bleeding by cauterizing the bleeding site contacting the distal end surface 6b and the living tissue surrounding the site.

Particularly, since the coagulation treatment can be carried out using a distal end surface 6b with a large contact area with the living tissue, the coagulation treatment can be performed reliably using the current for coagulation, while reducing energy density. Moreover, when this coagulation treatment is carried out, since the salient 9b is contained in the recess 6c, bleeding coagulation can be performed reliably by uniformly cauterizing the living tissue when the distal end surface 6b is pressed against. Furthermore, since the invasion of foreign materials and the like into the first electrode section 6 from the opening of the insertion hole 6a can be prevented, trouble due to contamination can be avoided.

Blood coagulation is carried out while performing the aforementioned coagulation treatment at appropriate times, and the circumferential incision of mucosa is carried out. After the circumferential incision, the submucosal layer is removed by cauterization and dissection using the second electrode section 9 again. Moreover, when bleeding is observed while performing this removal of the submucosal layer, coagulation treatment is carried out using the first electrode section 6, as described above. After completing the removal of the submucosal layer, a grasping forceps, for instance, is introduced via the instrument channel 4 and the affected area is grasped and separated from the digestive tract using the grasping forceps. Thereby, the affected area, including the submucosal layer, can be excised.

According to the high-frequency knife 1 of the present embodiment as described above, it is possible to perform dissection or coagulation treatment at appropriate times while rapidly switching from one treatment to another by mere movement control by the control section 8, without any need for interchanging instruments for dissection and coagulation or for switching plugs connected to the electrodes for dissection and coagulation as in the past. Thus, operation is easy and takes little time. Accordingly, the procedure time can be shortened and the burden on the patient can be reduced as much as possible. Moreover, when performing dissection or coagulation treatment, since electrode sections (the first electrode section 6 and the second electrode section 9) with appropriate shapes for the different treatments can be used separately and alternately with currents (currents for dissection and coagulation) with optimal frequencies, dissection and coagulation treatment can be carried out reliably.

Next, the second embodiment of the instrument for endoscope according to the present invention will be described below with reference to FIGS. 6 and 7. It should be noted that in this second embodiment, elements identical to those in the first embodiment are given the same symbols and descriptions thereof are omitted.

The difference between the first and second embodiments is that in the high-frequency knife 1 of the first embodiment, the first electrode section 6 is configured to electrically connect with the second electrode section 9 due to the outer circumferential surface of the salient 9b contacting the inner circumferential surface of the recess 6c when the second electrode section 9 is retracted into the first electrode section 6. On the other hand, in the high-frequency knife 30 of the second embodiment, the first electrode section 6 electrically connects with the second electrode section 9 via the stopper member 12 and a coil 31 when the second electrode section 9 retracts into the first electrode section 6.

Figure 6:
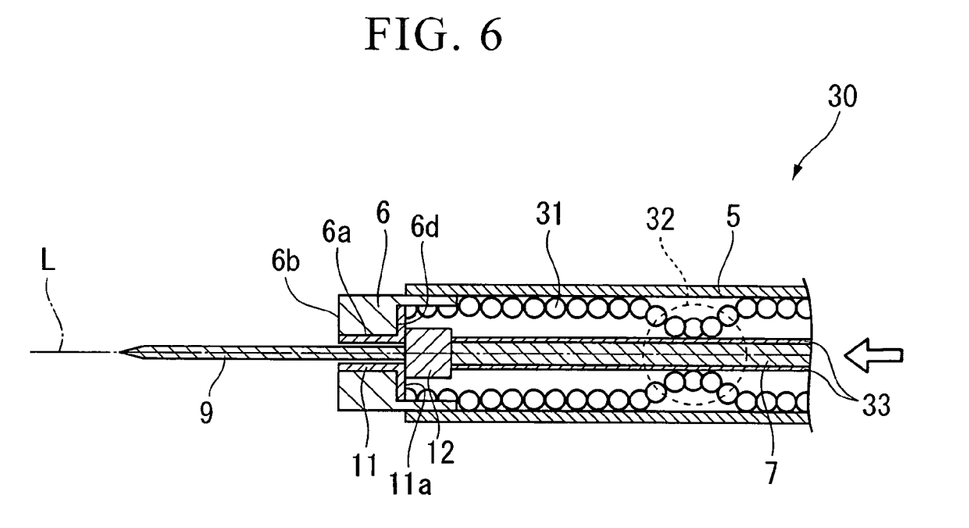
FIG. 6 is a diagram showing a second embodiment of the high-frequency knife according to the present invention and is an enlarged cross section of the distal end side where the second electrode section protrudes from the distal end of the first electrode section.
Figure 7:
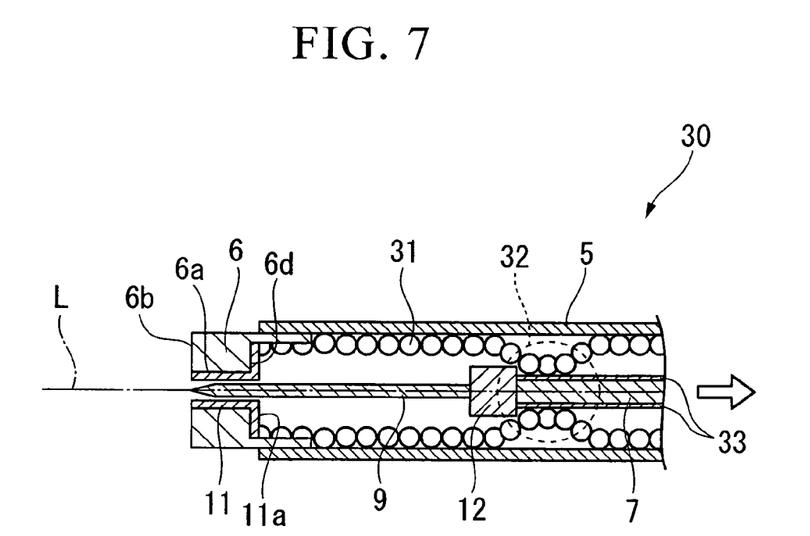
FIG. 7 is an enlarged cross section of the distal end side showing the state where the second electrode section is retracted into the first electrode section, following the state shown in FIG. 6.

That is, in the high-frequency knife 30 of the present embodiment, the coil 31 tightly coiled from the distal end side to the proximal end side is fixed onto the inner circumferential surface of the insertion section 5 as shown in FIGS. 6 and 7. The distal end thereof is connected to the first electrode section 6 while the proximal end thereof is connected to the distal end side of the control section main body 15. Moreover, in the coil 31, a diaphragm section 32 is provided which contacts the proximal end side of the stopper member 12 when the second electrode section 9 is completely retracted into the first electrode section 6. In other words, this diaphragm section 32 is configured so as to function as an electrically connecting section electrically connecting the stopper member 12 and first electrode section 6 when the second electrode section 9 is retracted. In addition, the second electrode section 9 of the present embodiment is a needle-shaped member with a pointed top.

Moreover, in the high-frequency knife 30 of the present embodiment, an insulating cover 33 covers the surroundings of the control wire 7. Therefore, the control wire 7 and coil 31 do not electrically contact when the current for dissection or coagulation is applied to the control wire 7, even if the insertion section 5 is bent. In particular, unintended electrical contact between the control wire 7 and diaphragm section 32 can be prevented.

When dissection treatment is carried out using the high-frequency knife 30 so configured, the area of contact with living tissue can be reduced since the second electrode section 9 is a needle-shaped member. Therefore, better sharpness can be ensured and thus, it is possible to dissect only the sites requiring dissection with high accuracy.

Moreover, when coagulation treatment is performed, the second electrode section 9 is retracted into the first electrode section 6 by moving the sliding section 16 to the proximal end side relative to the control section main body 15 as shown in FIG. 7. Then the stopper member 12 moves as a result of this operation and contacts the diaphragm section 32 of the coil 31. Note that the smoothness of the distal end surface 6b of the first electrode section 6 is ensured, since the second electrode section 9 completely retracts into the first electrode section 6 at the point where the stopper member 12 contacts the diaphragm section 32. In addition, after this state is reached, it is possible for the operator to know that the stopper member 12 and diaphragm section 32 are in contact by confirming that the movement of the sliding section 16 is regulated since the sliding section 16 will not move any further towards the proximal end side.

Then the current for coagulation is applied to the connecting cord 10 from the high-frequency power source 20 similarly to in the first embodiment. The current for coagulation is thereby applied to the first electrode section 6 via the control wire 7, stopper member 12, and coil 31. Note that the current for coagulation is also applied to the second electrode section 9 via the stopper member 12. Additionally, the current for coagulation applied to the coil 31 is reliably applied to the first electrode section 6 since the proximal end side of the coil 31 is connected to the non-conductive control section main body 15.

Accordingly, coagulation treatment can be carried out similarly to in the first embodiment by pressing the distal end surface 6b against living tissue. Furthermore, the high-frequency knife 30 of the present embodiment has improved strength against compression, tension, twist, and the like compared to the high-frequency knife 1 of the first embodiment since it is equipped with the coil 31. Thus, operability can be improved even more.

Figure 8:
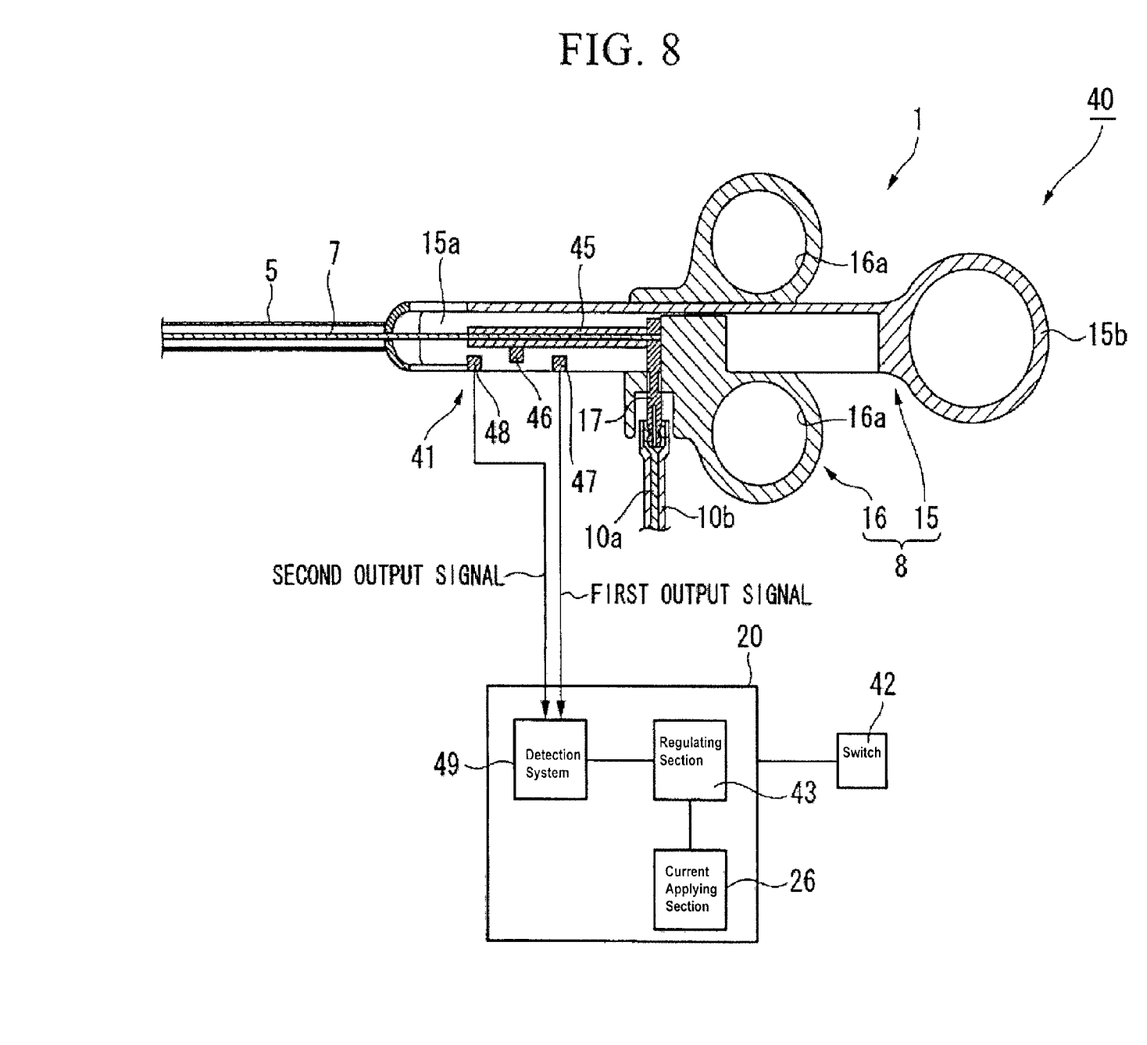
FIG. 8 is a configuration diagram showing one example of a high-frequency instrument system according to the present invention having the high-frequency knife of the first embodiment.

Next, the instrument system for an endoscope 40 according to the present invention having the high-frequency knife 1 of the first embodiment will be described by referring to FIG. 8.

The instrument system for an endoscope 40 of the present embodiment has the high-frequency knife 1, detection means 41 for determining the position of the sliding section 16 in the moving direction, a foot switch (switch) 42 for operating the current applying section 26 at an arbitrary time, and a regulating section 43 for automatically changing the current output settings of the current applying section 26 based on the determination made by the detection means 41. This regulating section 43 is internally installed in the high-frequency power source 20.

The detection means 41 has a wire cover 45 whose one end is connected to the sliding section 16 and covers the control wire 7, a plug 46 fixed in the outer circumferential surface of the wire cover 45, first and second detection sections 47 and 48 fixed on the control section main body 15 and provided in the proximal end side and distal end side of the control section main body 15 so as to position the plug 46 therebetween, and a detection section main body 49 electrically connected to the first and second detection sections 47 and 48 which receives output signals from the two detection sections 47 and 48.

The first detection section 47 is arranged at a position where it contacts the plug 46 when the sliding section 16 is moved to the proximal end side relative to the control section main body 15 and the salient 9b of the second electrode section 9 is contained in the recess 6c of the first electrode section 6, and configured so as to output first output signals to the detection section main body 49 upon contact. In addition, the second detection section 48 is arranged at a position where it contacts the plug 46 when the sliding section 16 is moved to the distal end side relative to the control section main body 15 and the stopper member 12 contacts the proximal end surface 11a of the insulating member 11, and configured so as to output second output signals to the detection section main body 49 upon contact.

The detection section main body 49 is internally installed in the high-frequency power source 20 and configured to determine the position of the sliding section 16 based on the first or second detection signals which are sent and inform the regulating section 43. In other words, the regulating section 43 can recognize whether the operator is going to perform dissection treatment or coagulation treatment beforehand. The regulating section 43 then automatically changes the current output settings of the current applying section 26 based on this information from the detection section main body 49.

That is, the regulating section 43 changes the current output settings of the current applying section 26 so that the current for dissection is applied when it is determined that the sliding section 16 has been moved to the distal end side and the plug 46 and second detection section 48 are in contact. On the other hand, the regulating section 43 changes the current output settings of the current applying section 26 so that the current for coagulation is applied when it is determined that the sliding section 16 has been moved to the proximal end side and the plug 46 and first detection section 47 are in contact. The current applying section 26 then applies current with the current output settings set by the regulating section 43 when the foot switch 42 is stepped on.

According to the instrument system for an endoscope 40 so configured, the operator can automatically apply current based on the position of the sliding section 16. That is, the current for dissection or coagulation can be supplied to the first electrode section 6 or second electrode section 9 by merely stepping on the foot switch 42 without any need to choose which current to apply based on the movement of the sliding section 16 while performing procedure. Thus, the operator can operate more easily and concentrate on the operation at hand since the current appropriate for procedure can be applied reliably without making mistakes. As a result, the safety of the procedure can be further enhanced.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

For instance, in each embodiment described above, although the inner circumferential surface and proximal end surface of the first electrode section are formed in an insulated state using the insulating member, they are not restricted to this and can be formed in an insulated state by being coated with insulative materials.

Moreover, the outer circumferential surface of the first electrode section can also be formed similarly in an insulated state when the first electrode section is configured to protrude from the distal end of the insertion section. By doing so, it is possible to further enhance safety since there is no problem even if the first electrode section and instrument channel or living tissue make contact when the current is applied to the first electrode section.

Figure 9:
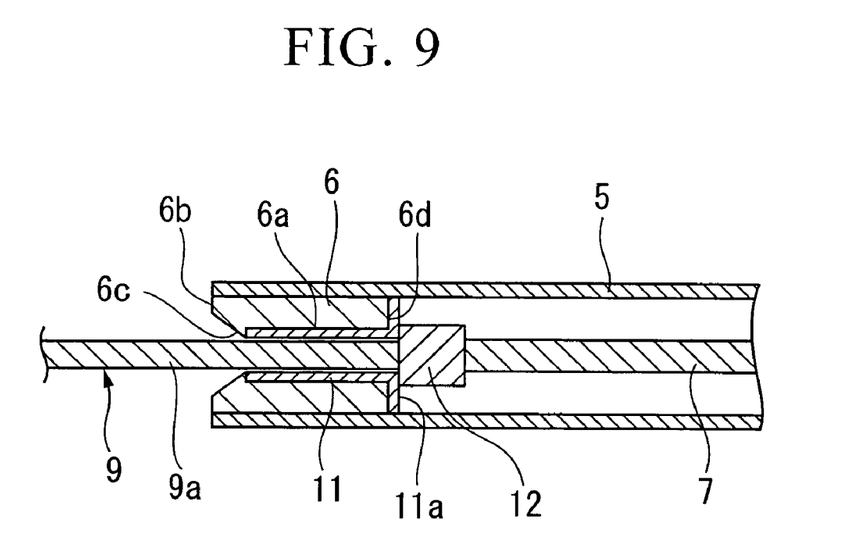
FIG. 9 is a cross section showing another example of the high-frequency knife of the first embodiment, where the high-frequency knife has an insertion section covering the entire outer circumferential surface of the first electrode section.

For example, it is possible to make the outer circumferential surface of the first electrode section 6 insulative by extending the insertion section 5 even further to the distal end side and configuring it so that it covers the outer circumferential surface, as shown in FIG. 9.

Figure 10:
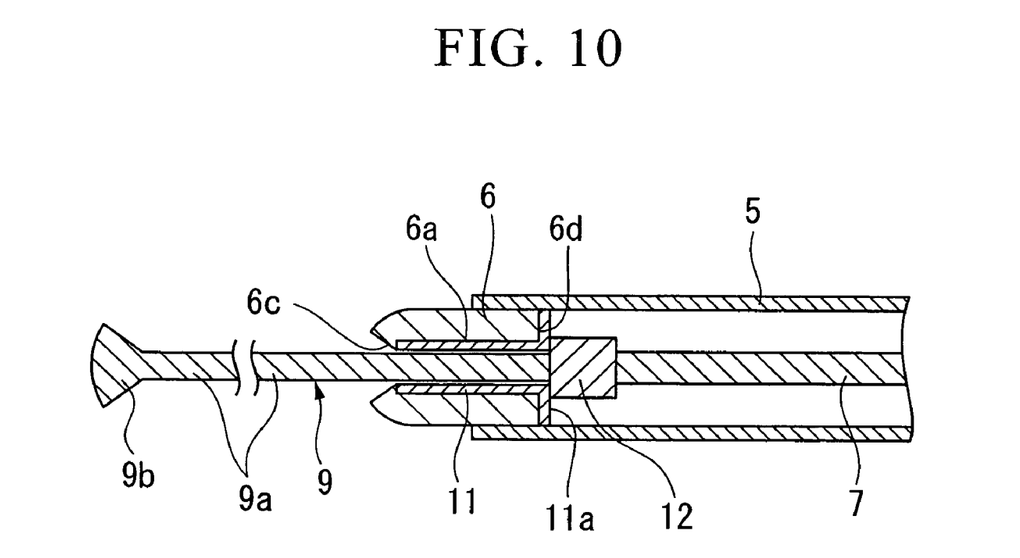
FIG. 10 is a cross section showing yet another example of the high-frequency knife of the first embodiment, where the high-frequency knife has a first electrode section whose distal end side is formed spherically.

Moreover, although the first electrode section is formed into a pipe shape with a circular section having a distal end surface in the above embodiments, the shape thereof is not limited to this. For instance, the distal end side can also be formed in a spherical shape, as shown in FIG. 10.

Figure 11:
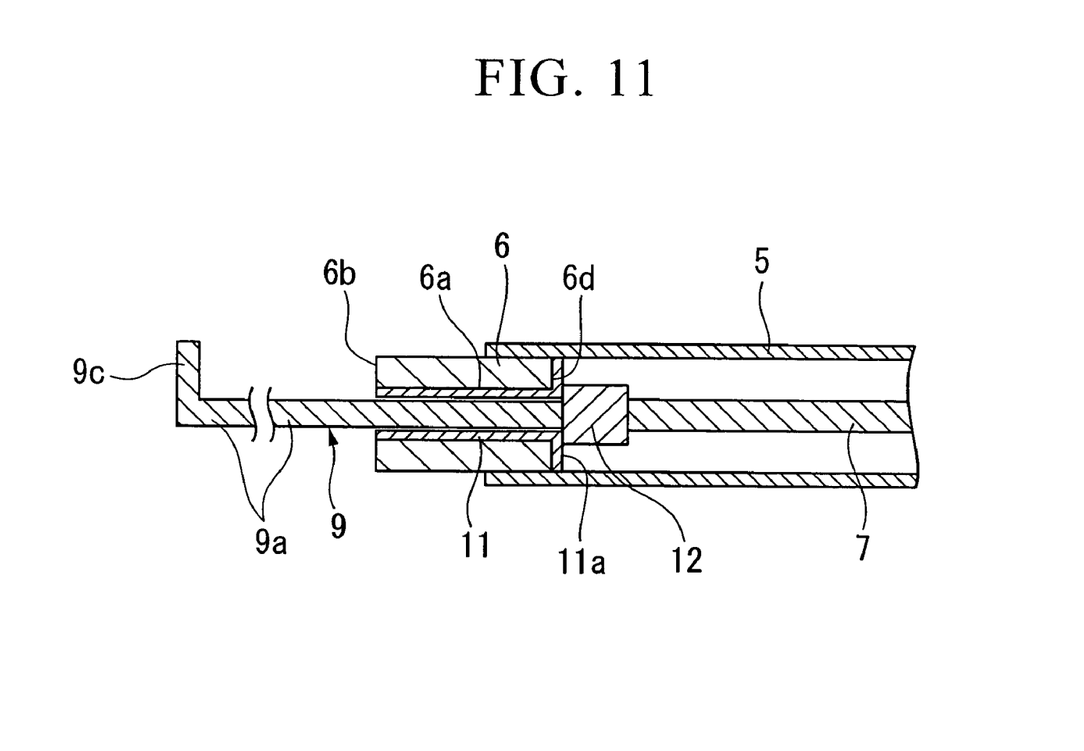
FIG. 11 is a cross section showing yet another example of the high-frequency knife of the first embodiment, where the high-frequency knife has a second electrode section with a bending section whose distal end is bent to an angle of almost 90 degrees.

Furthermore, although the second electrode section is formed in a shape with a salient at the distal end thereof or in a needle shape, the shape thereof is not limited to these. For instance, the shape can also be one with a bent section 9c whose distal end is bent by about 90 degrees, as shown in FIG. 11.

Figure 12:
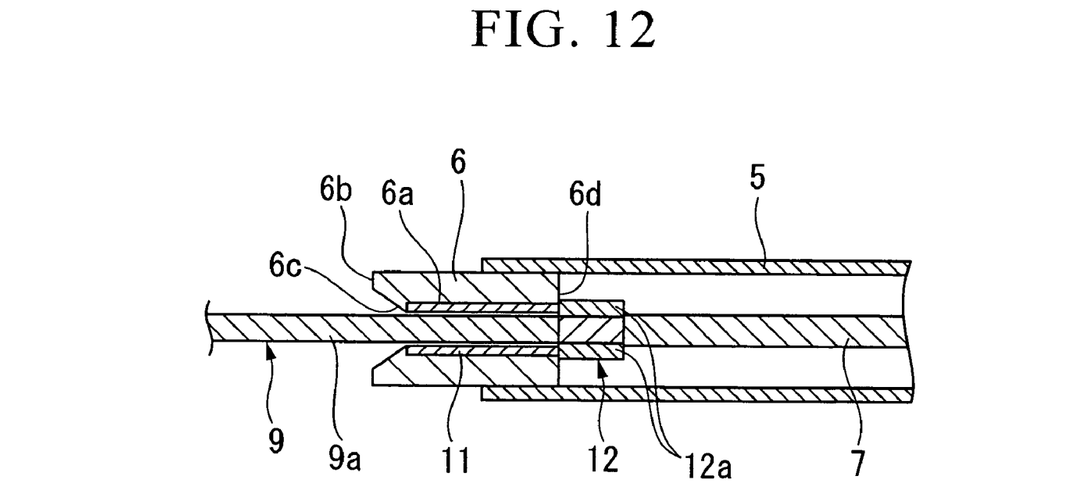
FIG. 12 is a cross section showing yet another example of the high-frequency knife of the first embodiment with an insulating region formed in a stopper member.

In addition, although the insulating member is arranged in the inner circumferential surface and proximal end surface of the first electrode section and the stopper member is made to provide insulation to the first electrode section when the second electrode section protrudes, the invention is not limited to this form. For example, as shown in FIG. 12, it is possible to arrange the insulating member 11 only on the inner circumferential surface of the first electrode section 6, and to form an insulating region 12a in the outer circumferential side of the stopper member 12 so that the stopper member 12 provides insulation to the first electrode section 6 when the stopper member 12 makes contact with the proximal end surface 6d of the first electrode section 6.

Figure 13:
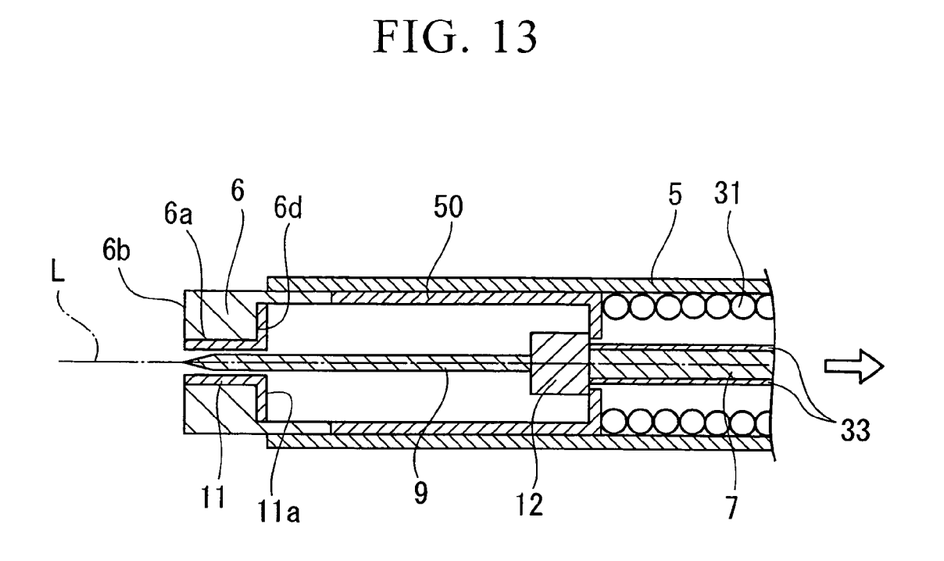
FIG. 13 is a cross section showing another example of the high-frequency knife of the second embodiment, where the stopper member and first electrode section electrically connect by way of a circular pipe when the second electrode section is retracted into the first electrode section.

Moreover, although the stopper member and the first electrode section are electrically connected using a coil in the second embodiment, other materials can be used. For instance, it is possible to fix a tubular pipe 50 which electrically connects the stopper member 12 and first electrode section 6 when the second electrode section 9 is retracted into the first electrode section 6 onto the inner circumferential surface of the insertion section 5, as shown in FIG. 13. It is also possible to form the proximal end side of the first electrode section 6 in such a way that it electrically contacts the stopper member 12 directly by extending further towards the proximal end side of the insertion section 5.

Figure 14:
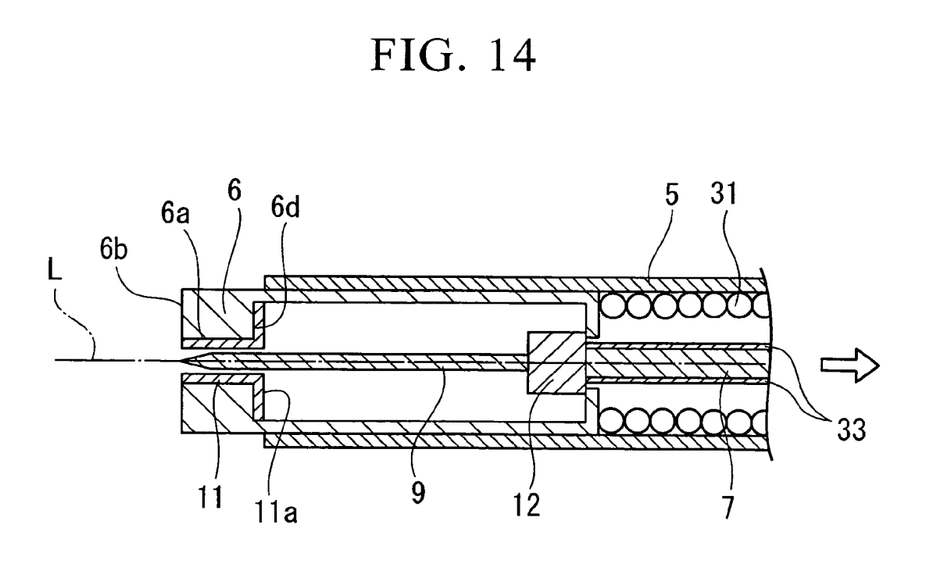
FIG. 14 is a cross section showing yet another example of the high-frequency knife of the second embodiment, where the proximal end side of the first electrode section is formed so as to extend toward the proximal end side of the insertion section and the first electrode section electrically connects with the stopper member directly when the second electrode section is retracted into the first electrode section.

There is the proviso, however, that use of a coil as the electrically connecting section as shown in the second embodiment is more preferable than any of the cases shown in FIGS. 13 and 14 from the viewpoints of flexibility and strength improvement of the insertion section.

Additionally, although a high-frequency instrument system having the high-frequency knife of the first embodiment is described, a high-frequency instrument system equipped with the high-frequency knife of the second embodiment is also possible.

What is claimed is:

1. An instrument for an endoscope comprising:
an insulative insertion section adapted to be inserted in a channel of an endoscope and having flexibility;
a tubular first electrode section arranged at a distal end of the insertion section and on which an insertion hole is formed along the axis of the insertion section;
a conductive electric wire inserted in the insertion section so as to be freely movable forwards and backwards;
a control section arranged on the proximal end side of the insertion section and controlling forward/backward movement of the electric wire along the axial direction;
a rod-shaped second electrode section connected to a distal end of the electric wire and inserted so as to be freely movable forwards and backwards inside the insertion hole;
an external connecting section electrically connected to a proximal end side of the electric wire and applying external currents with predetermined frequencies to the electric wire and the second electrode section;
a recess formed at the distal end of the first electrode section so as to surround the periphery of the opening of the insertion hole; and
a salient arranged at the distal end of the second electrode section and which extends in the direction perpendicular to the axial direction,
wherein the second electrode section protrudes from and retracts into the distal end of the first electrode section in response to the movement control by the control section, and also electrically connects with the first electrode section when retracted into the first electrode section when retracted into the first electrode section, and the salient is contained in the recess when the second electrode section retracts into the first electrode section.

2. The instrument for an endoscope according to claim 1, wherein the first electrode section is formed so that an inner circumferential surface thereof is in an electrically insulated state.

3. The instrument for an endoscope according to claim 1, further comprising a stopper member which is arranged between the electric wire and the second electrode section, which contacts the proximal end side of the first electrode section to regulate the extent of protrusion of the second electrode section when the second electrode section protrudes, and which provides insulation to the first electrode section when the stopper makes contact with the proximal end side of the first electrode section.

4. The instrument for an endoscope according to claim 1, wherein the first electrode section comprises a distal end surface parallel to the surface perpendicular to the axial direction.

5. The instrument for an endoscope according to claim 1, wherein the first electrode section is formed so that the entire outer circumferential surface is in an electrically insulated state.

6. An instrument system for an endoscope comprising:
an instrument for an endoscope according to claim 1,
detection means for determining the position of the control section in the moving direction;
a current applying section electrically connected to the external connecting section and applying the currents with predetermined frequencies;
a switch for operating the current applying section at an arbitrary time; and
a regulating section automatically changing the current output settings of the current applying section based on the determination made by the detection means.

* * * * *